United States Patent [19]

Boor

[11] Patent Number: 5,771,841

[45] Date of Patent: Jun. 30, 1998

[54] SANITATION SYSTEM FOR ANIMAL CAGES

[76] Inventor: Jonathan Jarrett Boor, 2931 NE. 39th Ct., Lighthouse Point, Fla. 33064

[21] Appl. No.: 835,756

[22] Filed: Apr. 8, 1997

Related U.S. Application Data

[60] Provisional application No. 60/015,058 Apr. 9, 1996.

[51] Int. Cl. [6] .................................................. A01K 29/00
[52] U.S. Cl. ............................................................. 119/452
[58] Field of Search .................................. 119/452, 458, 119/163, 165

[56] References Cited

U.S. PATENT DOCUMENTS

| | | |
|---|---|---|
| 3,177,848 | 4/1965 | Rubricius . |
| 3,318,285 | 5/1967 | Betham .................................. 119/163 |
| 3,343,522 | 9/1967 | Biehl . |
| 3,658,031 | 4/1972 | Coe . |
| 3,662,713 | 5/1972 | Sachs . |
| 3,822,673 | 7/1974 | Benny . |
| 3,828,732 | 8/1974 | Hill et al. . |
| 3,842,803 | 10/1974 | Temel ..................................... 119/165 |
| 3,896,768 | 7/1975 | Galloway . |
| 3,900,006 | 8/1975 | Shockley, Jr. . |
| 3,978,819 | 9/1976 | Lovitt . |
| 3,991,717 | 11/1976 | Buchanan ............................... 119/165 |
| 4,009,685 | 3/1977 | Sojka . |
| 4,011,835 | 3/1977 | Temel ......................................... 119/1 |
| 4,173,947 | 11/1979 | Whiteside, Jr. . |
| 4,206,720 | 6/1980 | Ruggeri et al. . |

*Primary Examiner*—Thomas Price
*Attorney, Agent, or Firm*—Shoemaker and Mattare, Ltd.

[57] ABSTRACT

A small animal cages has a mulch or litter drawer and a drain pan below the mulch drawer, and a spray head between the drain pan and the mulch drawer, for spraying the drawer from below. An ultraviolet light is also disposed between the drain pan and the drawer, to sterilize the drawer after it is washed. Wash, rinse, and illumination steps are carried out automatically by a programmable timer. The wash and rinse water is captured and disposed of as required by law.

15 Claims, 3 Drawing Sheets

SANITATION SYSTEM FOR ANIMAL CAGES

This application relates to provisional application 60/015,058, filed Apr. 9, 1996.

BACKGROUND OF THE INVENTION

This invention relates to the art of animal husbandry, and more particularly to a sanitation system for cages for animals such as laboratory rodents.

To maintain animals in cages properly, one must expend significant time and effort cleaning the cages, so as to minimize biological contamination of the environment, other animals at the facility, and people in the vicinity. The development of acceptable cleaning and sterilizing programs, plus the training and supervision of assistants to carry out the programs, has labor costs, and detracts from other tasks. Such programs are essential, however, to protect animals, humans, and the environment generally.

Prior inventors have proposed numerous ways of automatically maintaining small animal cages in a clean condition. Representative patents are U.S. Pat. Nos. 3,343,522, 3,177,848, 3,658,031, 3,662,713, 3,822,673, 3,828,732, 3,896,768, 3,978,819 and 4,009,685. Typically, the cages are sprayed with water or a solution which falls onto a collection tray or trough. Water flow may be controlled by electrically operated valves and a timer.

Other inventors have provided cage systems with illumination for various purposes, and with fans to provide ventilation. See U.S. Pat. No. 3,900,006, for example.

SUMMARY OF THE INVENTION

An object of this invention is to provide an improved sanitation system for cages for laboratory animals and the like.

Another object is to eliminate or minimize bacterial transfer to humans working with small animals.

A further object is to increase the efficiency of laboratory workers, and thus reduce associated labor costs.

Yet another object of the invention is to provide procedures for cleaning, rinsing, drying and sterilizing animal cages.

These and other objects are attained by a sanitation system for animal cages having mulch or litter drawers, comprising a drain pan below the mulch drawer, an irrigation system for washing and rinsing the drawer from below, an ultraviolet light between the drain pan and the drawer for disinfecting the cage, and a fan for drying the cage while it is being disinfected. The elements of the systems are operated automatically in sequence by a programmable controller.

DESCRIPTION OF THE PREFERRED EMBODIMENT

Figure 1:
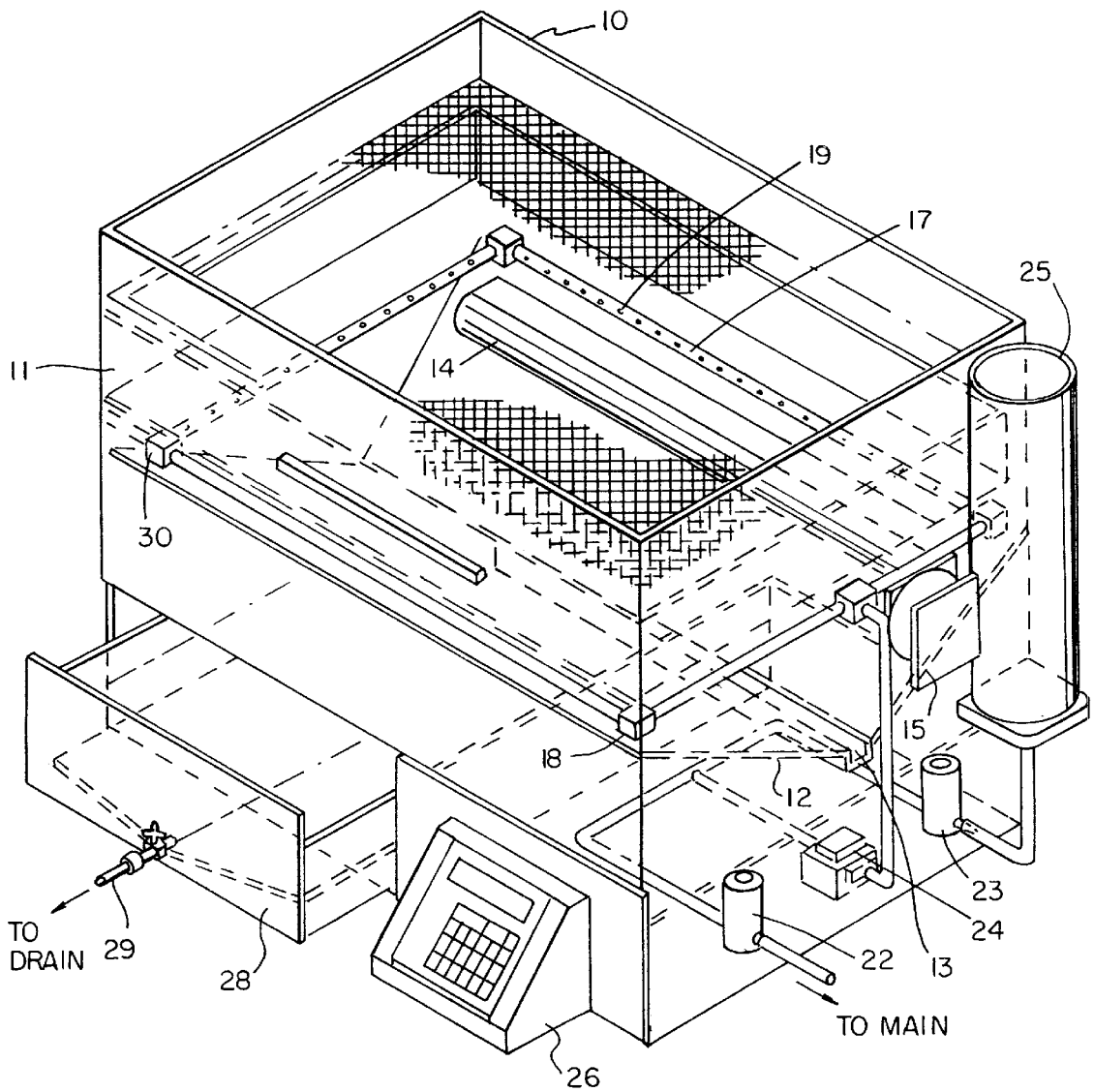
FIG. 1 is an exploded isometric view of an animal cage 11 embodying the invention.
Figure 2:
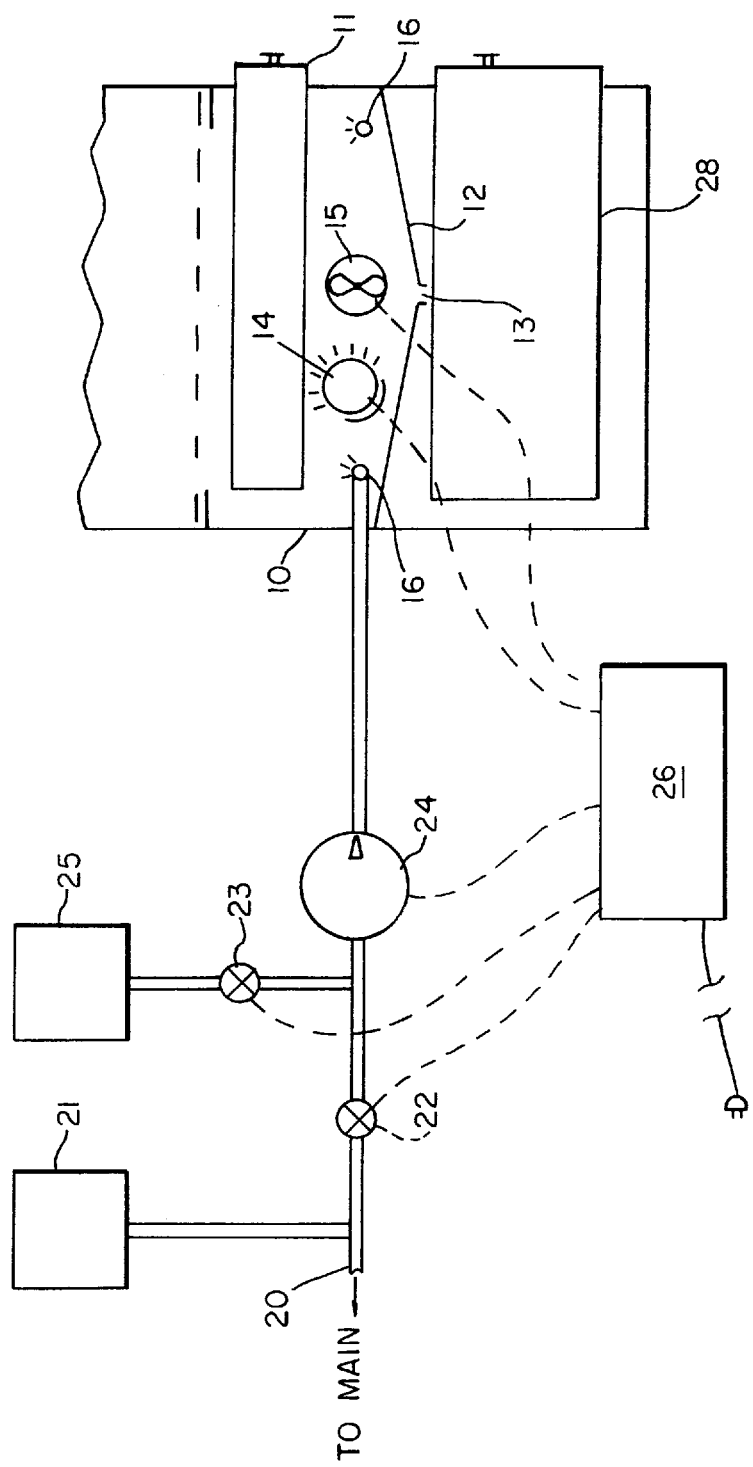
FIG. 2 is a simplified side sectional view of the cage, with the plumbing and electrical circuits shown diagrammatically.

An apparatus embodying the invention, as shown in the drawing, includes a cage bottom 10 (the top portion having been removed in the drawing) containing a removable mulch tray 11 which may pulled out, as indicated by the arrow, and removed to dispose of litter. The tray is designed so that it can be replaced in the case upside down, as discussed below.

A drain pan 12 having a central drain 13 is positioned below the tray. The pan illustrated has four segments, all sloping inward toward the drain, but other configurations are possible.

An ultraviolet lamp 14 is mounted on the side of the cage, above the drain pan and below the litter tray, so that it can illuminate the pan and the bottom of the tray. The lamp selected is one which will provide illumination at a wavelength of about 254 nm, at an intensity of at least 8700 microwatt/cm$^2$. An eight-watt GE bulb #FHT5-BLB in a suitable fixture has been found adequate for small animal cages.

A three-inch diameter electric 35 CFM axial-flow fan 15 is mounted at the side of the cage, and electrically connected in parallel with the bulb. The fan helps dry the cage after it is washed, as described below.

A spray head 16, comprising four perforated pipes 17 interconnected by elbows 18 to form a rectangle slightly smaller than the plan cross-section of the cage, is supported by attachments (not shown) to the cage, just above the drain pan 12. An array of small holes 19 in the pipe wall are directed upward, at the bottom of the tray.

The piping is preferably a transparent plastic tubing such as Excelon R-4000 clear rigid pipe, manufactured by Industrial Thermoplastic Solutions.

Water is supplied to the spray head by a plumbing system at the bottom of the cage. Reference numeral 20 indicates a fresh water supply line, shown entering the cage at the bottom. Numerals 22 and 23 identify solenoid-actuated two-way flow control valves: the former controls fresh water flow from the water supply to the pump 24, while the latter controls the injection of disinfectant or detergent from a supply container 25 into the water line. The bottle may be provided with a volumetric gauge or with a flow rate gauge, neither of which is shown.

The preferred pump is an oscillating-piston pump having an electric motor, with a maximum delivery pressure of about 72 psi and a maximum flow rate of about one-half gallon per minute.

A preferred disinfectant is sold under the trademark Synphenol-3 by Farnam Companies, Inc. It is a synthetic detergent with a broad bacteriocidal spectrum. This disinfectant is diluted at the rate of ½ ounce per gallon of water. A ½-gallon bottle 25 is then filled with this solution, and installed on the cage in the inverted position shown. When the valve 23 is open, the solution is delivered under pressure by the pump 24 to the spray head, where it is discharged through the orifices 19, cleaning and sterilizing the mulch drawer and the cage bottom. Subsequently, when the valve 22 is open, fresh water is delivered under pressure to the spray head. The fresh water supply bottle 21 is optional.

The valves 22 and 23 are operated by a programmable control unit 26, which includes a timer, and has plural independent electrical outputs. A suitable unit is an electronic control timer #63-891, manufactured by Micronta, which normally runs from 110 V.A.C. line current, but has a 9V alkaline battery backup. The unit is electrically connected to the electric motor of the piston pump, and to the valves 22 and 23, and is then programmed so that at established intervals, it activates the valves to flush waste and debris from the drain pan, according to the schedule described below. The ultraviolet light is also controlled by the timer.

Figure 3:
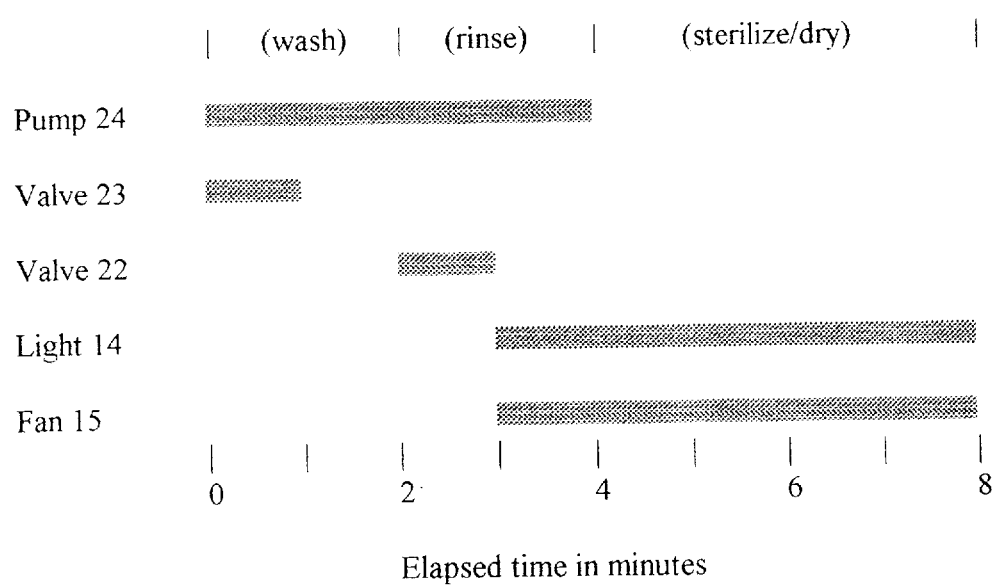
FIG. 3 is a bar graph illustrating the operating cycle of the system.

To clean the cage, one first withdraws the tray from the cage, and discards the mulch and animal waste upon it. The tray is then inverted and reinserted into the cage, and the controller is activated to clean the cage. The controller will have been programmed so as to provide wash, rinse and disinfect cycles as shown in FIG. 3. The programming steps are matters of ordinary skill.

During the wash cycle, first the valve 23 is opened, so that the bottom of the cave and the tray are sprayed with a detergent/disinfectant solution, delivered at 72 psi by the pump, for one minute at a rate of about one-half gallon per minute. The detergent supply is cut off at the one minute point, but the pump continues to run for another minute to flush the line. Waste water and debris from the litter tray fall onto the drain pan, and out through the drain to a removable receiver such as the bottom tray 28 (FIG. 1), which may have a flexible drain line 29, as illustrated, leading to a remote waste receiver.

After the washing interval, the valve 22 is opened, and the cage is rinsed with potable water, again at the rate of one-half gallon per minute. In the middle of the rinse cycle (i.e., at the three minute point), the valve 22 is closed and the ultraviolet germicidal lamp 14 is turned on, and kept on for five minutes. The fan 15 is on the same circuit with the bulb, and so runs during the illumination period, drying the bottom of the cage. Thus the total duration of the automatic sterilization cycle is eight minutes. This compares favorably with manual cleaning, which usually takes twelve to fifteen minutes, in part because of the time required to prepare the worker and to protect him from contamination.

After the sterilization cycle is complete, the tray is removed, and then replaced after new mulch has been placed upon it.

In a laboratory or other setting where a number of like cages are present, neighboring cages may be interconnected by tees 30 or other suitable plumbing fittings as suggested by FIG. 1. With cages thus connected, a single controller can be used to clean all the cages at once. Obviously, the volumetric capacity of the pump in the master cage must be scaled up to produce the increased flow required, and the plumbing may have to be modified to handle the increased flow rate.

Similarly, the lamps and fans for all the cages in the array are electrically interconnected so as to operate in unison when energized by the common controller. The advantage of grouping cages this way is that the electrical controls and valving may be eliminated from all but the master cage.

Although the cases described are intended for small animals, it should be understood that the invention is not limited to use with cages of a particular size. With mere changes in size and possibly materials, the invention could be scaled up for cages for much larger animals.

Inasmuch as the invention is subject to modifications and variations, it is intended that the foregoing description and the accompanying drawings shall be regarded as merely illustrative of the invention defined by the following claims.

I claim:

1. An animal cage comprising:

a removable litter tray and means for supporting the litter tray in the cage, the tray being designed so that it can be removed, inverted and reinserted into t cage, a spray head below the litter tray, said spray head having nozzle orifices for directing cleaning liquid upward against the tray, a source of cleaning liquid, means for pumping said liquid under pressure to said spray head, a drain pan below the spray head, to catch cleaning liquid dropping from the litter tray, an ultraviolet lamp disposed below the litter tray for disinfecting the tray, and programmable means for operating the pumping means and the ultraviolet lamp in sequence, so as to first wash the tray and then sterilize it.

2. The invention of claim 1, further comprising a fan for blowing air over the litter tray, and means for operating the fan while the lamp is on, to dry the tray as it is sterilized.

3. The invention of claim 1, further comprising a water line for delivering water from a water supply to the pump.

4. The invention of claim 3, further comprising a container for a water additive, and means for delivering said additive from the container to said water line.

5. The invention of claim 4, wherein the additive is a detergent.

6. The invention of claim 4, wherein the additive is a disinfectant.

7. The invention of claim 4, further comprising a first electrically controlled valve for controlling flow of water from said source through said water line to said pumping means.

8. The invention of claim 4, further comprising an electronic controller for operating said valves, said lamp, and said fan in a predetermined sequence.

9. The invention of claim 1, further comprising a receiver for containing used process water, said receiver being removable from the cage.

10. A method of cleaning and disinfecting animal cages having removable litter trays, said method comprising steps of:

removing the litter tray and discarding any litter on it, reinserting the litter tray into the cage, spraying the cage and the tray from below with a cleaning liquid, illuminating the cage and tray with ultraviolet light to disinfect the cage and tray, drying the tray in place, and placing fresh litter on the tray.

11. A method of cleaning and disinfecting animal cages having removable litter trays, said method comprising steps of:

removing the litter tray and discarding any litter on it, inverting the tray and reinserting it into the cage, spraying the tray from below with a cleaning liquid, illuminating the tray with ultraviolet light to disinfect the tray, drying the tray in place, removing the tray and reinverting it, placing fresh litter on the tray, and reinserting the tray in the cage.

12. The invention of claim 11, wherein the spraying step comprises two phases: a washing phase which the cleaning liquid is water plus an additive, and a rinsing phase in which the cleaning liquid is water only.

13. The invention of claim 12, wherein the additive is a detergent/disinfectant solution.

14. The invention of claim 12, wherein the washing step has a duration of about two minutes, the rinsing step has a duration of about two minutes, and the illumination step has a duration of about five minutes.

15. The invention of claim 14, wherein the illuminating step overlaps the rinsing phase, but not the washing phase.

* * * * *